(12) United States Patent
Averback

(10) Patent No.: US 12,329,802 B2
(45) Date of Patent: *Jun. 17, 2025

(54) FOCAL TREATMENT OF PROSTATE CANCER

(71) Applicant: Nymox Corporation, New Providence (BS)

(72) Inventor: Paul Averback, Nassau (BS)

(73) Assignee: NYMOX CORPORATION, Nassau (BS)

(*) Notice: Subject to any disclaimer, the term of this patent is extended or adjusted under 35 U.S.C. 154(b) by 163 days.

This patent is subject to a terminal disclaimer.

(21) Appl. No.: 17/740,755

(22) Filed: May 10, 2022

(65) Prior Publication Data

US 2022/0323543 A1 Oct. 13, 2022

Related U.S. Application Data

(63) Continuation of application No. 16/528,326, filed on Jul. 31, 2019, now Pat. No. 11,331,374.

(51) Int. Cl.
*A61K 38/17* (2006.01)
*A61K 45/06* (2006.01)
*A61P 35/00* (2006.01)

(52) U.S. Cl.
CPC .......... *A61K 38/1761* (2013.01); *A61P 35/00* (2018.01); *A61K 45/06* (2013.01)

(58) Field of Classification Search
CPC .................. A61K 38/1761; A61P 35/00
See application file for complete search history.

(56) References Cited

U.S. PATENT DOCUMENTS

| | | | |
|---|---|---|---|
| 4,457,489 | A | 7/1984 | Gilmore |
| 6,924,266 | B2 | 8/2005 | Averback |
| 7,172,893 | B2 | 2/2007 | Rabinowitz et al. |
| 7,192,929 | B2 | 3/2007 | Averback |
| 7,241,738 | B2 | 7/2007 | Averback et al. |
| 7,317,077 | B2 | 1/2008 | Averback et al. |
| 7,408,021 | B2 | 8/2008 | Averback et al. |
| 7,745,572 | B2 | 6/2010 | Averback et al. |
| 8,067,378 | B2 | 11/2011 | Averback et al. |
| 8,293,703 | B2 | 10/2012 | Averback et al. |
| 8,569,446 | B2 | 10/2013 | Averback et al. |
| 8,716,247 | B2 | 5/2014 | Averback et al. |
| 9,243,035 | B2 | 1/2016 | Averback et al. |
| 2007/0237780 | A1 | 10/2007 | Averback |
| 2016/0215031 | A1 | 12/2016 | Averback |
| 2017/0020957 | A1 | 1/2017 | Averback |
| 2017/0360885 | A1* | 12/2017 | Averback ........... A61K 38/1709 |

OTHER PUBLICATIONS

Nymox. Two-dose level evaluation of NX-1207 for the treatment of low risk, localized (T1c) prostate cancer. Available from https://clinicaltrials.gov/ct2/show/NCT01620515. NLM Identifier: NCT01620515, first posted Jun. 15, 2012 (Year: 2012).*
S. Altschul et al. "Basic Local Alignment Search Tool", J. Mol. Biol., 215: 403-410 (1990).
Humberto Carrillo et al., "The Multiple Sequence Alignment Problem in Biology", Siam, J. Applied Math., vol. 48, No. 5, Oct. 1988, pp. 1073-1082.
J. Couder et al., "Synthesis and Biological Activities of φ(Ch2NH) Pseudopeptide analogies of the C-terminal Hexapeptide of neurotensin" Int. J. Peptide Protein Res., 41:181-184, 1993.
Alma Dalpozzo et al. "H-Gly-Hisw(NHCO) Lys-OH, partially modified retro-inverso analogue of the growth factor Glycyl-L-histidyl-L-lysine with enhanced enzymatic stability", (1993), Int. J. Peptide Protein Res., 41:561-566.
J. Devereux, et al., "A Comprehensive set of Sequence Analysis Programs for the VAX", Nucleic Acids Research, 12(1): 387-395 (1984).
E. J. Freireich et al., "Quantitative Comparison of Toxicity of Anticancer Agents in Mouse, Rat, Hamster, Dog, Monkey, and Man", Cancer Chemother. Rep., vol. 50, No. 4, pp. 219-244 (May 1966).
Steven Henikoff et al., "Amino Acid Substitution Matrices from Protein Blocks", Proc. Natl. Acad. Sci USA, 89:10915-10919, Nov. 1992.
Suresh I.S. Rattan et al., "Protein Synthesis: Posttranslational Modifications and Aging," Ann. N.Y. Acad. Sci. 663: 48-62 (1992).
Scientific Tables, Geigy Pharmaceuticals, Ardsley, N.Y. pp. 537-538 (1970).
Sam Seifter et al., "[47] Analysis for Protein Modifications and Nonprotein Cofactors", Methods in Enzymology, vol. 182 pp. 626-646 (1990).
Reyna J. Simon et al., "Peptoids: A modular approach to drug discovery", Proc. Natl. Acad. Sci. USA, vol. 89, pp. 9367-9371, Oct. 1992.
A. Sisto et al. in Rivier, J. E. and Marshall, G. R., "Biologically active retro-inverso analogs of thymopentin", Peptides, Chemistry, Structure and Biology, Escom, Leiden (1990), pp. 722-773.
Smith Craig C. et al., "Tritiated D-ala.sup.1-Peptide T Binding", Drug Development Res., 15, pp. 371-379 (1988).
Gunnar Von Heijne, "Chapter 6, Sequence Similarities, Homologies, and Alignments", Sequence Analysis in Molecular Biology, p. 123-139 Academic Press, New York, N.Y. 1987.
Wold, F., "Posttranslational Protein Modifications: Perspectives and Prospects," pp. 1-12 in Posttranslational Covalent Modification of Proteins, B. C. Johnson, Ed., Academic Press, New York (1983).

(Continued)

*Primary Examiner* — Vanessa L. Ford
*Assistant Examiner* — Sandra Carter
(74) *Attorney, Agent, or Firm* — Pillsbury Winthrop Shaw Pittman, LLP

(57) ABSTRACT

The embodiments include methods of treating prostate cancer by administering to a low grade unifocal prostate cancer tumor a composition comprising a therapeutically effective amount of pharmaceutically active ingredient capable of inducing necrosis of a low grade unifocal prostate cancer tumor, wherein administration reduces cancer incidence, cancer grade, and cancer progression (worsening) in the entire hemi-prostate where the initial focus was located and treated.

11 Claims, No Drawings

Specification includes a Sequence Listing.

(56) References Cited

OTHER PUBLICATIONS

Ruth Etzioni et al., "Asymptomatic Incidence and Duration of Prostate Cancer", Am J Epidemiol. vol. 148, No. 8, pp. 775-785 (1998).
Roman Gulati et al., "What If I Don't Treat My PSA-Detected Prostate Cancer? Answers from Three Natural History Models", Cancer Epidemiol Biomarkers Prev; 20(5), pp. 740-750, May 2011.
Roberta Mazzucchelli et al., "Pathology of Prostate Cancer and Focal Therapy ('Male Lumpectomy')", Anticancer Research, vol. 29, pp. 5155-5162 (2009).
Chinyere Ibeawuchi et al., "Genome-Wide Investigation of Multifocal and Unifocal Prostate Cancer—Are They Genetically Different?" Int. J. Mol. Sci., vol. 14, pp. 11816-11829 (2013).
Philip Quann et al., "Current prostate biopsy protocols cannot reliably identify patients for focal therapy: correlation of low-risk prostate cancer on biopsy with radical prostatectomy findings", Int. J. Clin. Exp. Pathol., 3(4), pp. 401-407 (2010).
M.O. Dayhoff et al. "22 A Model of Evolutionary Change in Proteins", Atlas of Protein Sequence and Structure, vol. 5, supp. 3, pp. 345-352, (1978).
Hashim Uddin Ahmed et al., "Do Low-Grade and Low-Volume Prostate Cancers Bear the Hallmarks of Malignancy," www.thelancet.com/oncology, vol. 13, pp. e509-e517 (Nov. 2012).
Neal Shore et al., "The potential for NX-1207 in benign prostatic hyperplasia: an update for clinicians," Ther. Adv. Chronic Dis., 2(6), pp. 377-383 (2011).
Nymox (Nymox reports 5-year results from prospective randomized controlled prostate cancer study of fexapotide triflutate in 146 US men. (2018). BioSpace, retrieved from https://dialog.proquest.com/professional/docview1990801632?accountid=131444). (Year 2018).
International Search Report & Written Opinion of the International Searching Authority dated Dec. 4, 2020 issued in corresponding International Patent Application No. PCT/US2020/044192 (16 pgs.).
Anonymous, "Nymox Announces Prostate Cancer Clinical Trial Results From Completed 18 Month Endpoint Study", Feb. 9, 2016, XP055404013, Retrieved from the Internet: URL:http://money.cnn.com/news/newsfeeds/articles/globenewswire/6174512.htm, retrieved Feb. 4, 2021.
Neal Shore et al., "Efficacy and safety of fexapotide triflutate in outpatient medical treatment of male lower urinary tract symptoms associated with benign prostatic hyperplasia", Therapeutic Advances in Urology, 2019, vol. 11, pp. 1-16.
Mazzucchelli et al. Anticancer Research 29: 5155-5162 (2009) (Year: 2009).
Shore et al. Ther Adv Ural. Jan.-Dec. 2019; 11: 1756287218820807 (Year: 2019).
International Preliminary Report on Patentability dated Nov. 15, 2021, issued in corresponding International Patent Application No. PCT/US2020/044192 {23 pgs.).

* cited by examiner

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Ile Asp Gln Gln Val Leu Ser Arg Ile Lys Leu Glu Ile Lys Arg Cys
1               5                   10                  15

Leu

FOCAL TREATMENT OF PROSTATE CANCER

CROSS REFERENCE TO RELATED APPLICATIONS

This application is a Continuation Application of U.S. Ser. No. 16/528,326, filed Jul. 31, 2019, the subject matter of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 31, 2019, is named NYMOX-0505230_ST25.txt and is 474 bytes in size.

BACKGROUND

1. Field of the Embodiments

The embodiments include methods of treating prostate cancer in mammals having prostate cancer, and more specifically to methods of preventing and/or reducing multifocal prostate cancer development and progression by administering to a low grade, low risk, localized (T1c) prostate cancer tumor a composition comprising a pharmaceutically active ingredient capable of inducing necrosis of the low grade, low risk, localized prostate cancer tumor and a pharmaceutically acceptable carrier. In one embodiment, the pharmaceutically active ingredient is fexapotide triflutate ("FT"). The methods include, but are not limited to, administering the compositions intramuscularly, orally, intravenously, intraperitoneally, intraprostatically, intracerebrally (intraparenchymally), intracerebroventricularly, intralesionally, intraocularly, intraarterially, intrathecally, intratumorally, intranasally, topically, transdermally, subcutaneously, or intradermally to patients in need thereof, wherein targeted administration of the compositions to the low grade, low risk, localized (T1c) prostate cancer tumor reduces prostate cancer incidence, in prostate cancer grade, and in prostate cancer progression (worsening) throughout the entire hemi-prostate where the initial unifocal tumor was located and treated.

2. Description of Related Art

The essence of many medical treatments and procedures involves the removal or destruction of harmful or unwanted tissue. Examples of such treatments include the surgical removal of cancerous or pre-cancerous growths, the destruction of metastatic tumors through chemotherapy, and the reduction of glandular (e.g. prostate) hyperplasia. Other examples include the removal of unwanted facial hair, the removal of warts, and the removal of unwanted fatty tissue.

There is a need for an effective composition that will destroy and hence either facilitate the removal of or inhibit the further growth of harmful or unwanted cells and tissue but will have mainly local effects and minimal or absent systemic toxicity. There also is a need to reduce the need for invasive surgical intervention, even after treatment with an effective composition.

Some agents known to have the ability to destroy and hence either facilitate the removal of or inhibit the further growth of harmful or unwanted cells and tissue are disclosed in U.S. patent application Ser. No. 14/808,713, filed Jul. 24, 2015, entitled: METHODS OF REDUCING THE NEED FOR SURGERY IN PATIENTS SUFFERING FROM BENIGN PROSTATIC HYPERPLASIA; U.S. patent application Ser. No. 14/606,683, filed Jan. 27, 2015, entitled: METHOD OF TREATING DISORDERS REQUIRING DESTRUCTION OR REMOVAL OF CELLS, U.S. application Ser. No. 14/738,551, filed Jun. 12, 2015, entitled: COMBINATION COMPOSITIONS FOR TREATING DISORDERS REQUIRING REMOVAL OR DESTRUCTION OF UNWANTED CELLULAR PROLIFERATIONS, U.S. patent application Publication Nos. 2007/0237780 (now abandoned); 2003/0054990 (now U.S. Pat. No. 7,172,893); 2003/0096350 (now U.S. Pat. No. 6,924,266); 2003/0096756 (now U.S. Pat. No. 7,192,929); 2003/0109437 (now U.S. Pat. No. 7,241,738); 2003/0166569 (now U.S. Pat. No. 7,317,077); 2005/0032704 (now U.S. Pat. No. 7,408,021); and 2015/0148303 (now U.S. Pat. No. 9,243,035), the disclosures of each of which are incorporated by reference herein in their entirety.

One of the agents disclosed in these documents is fexapotide triflutate, or FT. FT has been shown to reduce prostate glandular cells, to ameliorate or reduce LUTS, and to treat BPH in men with prostate enlargement. FT also has been disclosed as useful in reducing the onset of prostate cancer by treating BPH in a mammal having BPH in which the compositions containing FT are administered to the mammal in transition zone (central) prostate. See, e.g., U.S. Pat. No. 10,183,058, the disclosure of which is incorporated by reference herein in its entirety.

Prostate cancer is known as a disease with an extremely high prevalence relative to its clinical incidence in the population. Prostate cancer has a high asymptomatic incidence and a long asymptomatic duration. Prostate cancer has an interval of 7 to 14 years on average during which the cancer is present but is preclinical because it is not detected by typical clinical or laboratory examinations (see Etzioni, R et al., *Am J Epidemiol*. Vol. 148, pp. 775-85 (1998); and Gulati, R, et al., *Cancer Epidemiol Biomarkers Prev*; Vol. 20(5), pp. 740-50 (2011)). These preclinical asymptomatic prostate cancers prior to their overt diagnosis are a reasonable target for treatment which can benefit patients before the cancers have become clinically apparent or detected otherwise.

Prostate cancer is often considered a multifocal disorder in which the prostate gland includes multiple adenocarcinoma foci of varying heterogeneity. This makes the cancer difficult to treat effectively, often resulting in radical prostatectomy, which causes numerous life altering issues for men including erectile dysfunction and urinary incontinence. Some prostate cancers, however, or unifocal prostate cancer, which has been reported in from about 20 to about 35% of radical prostatectomy specimens. Mazzucchelli, et al., "Pathology of Prostate Cancer and Focal Therapy ('Male Lumpectomy')," *Anticancer Research*, Vol. 29, pp. 5155-5162 (2009); Ibeawuchi, et al., "Genome-Wide Investigation of Multifocal and Unifocal Prostate Cancer—Are They Genetically Different?" *Int. J. Mol. Sci.*, Vol. 14, ppp. 11816-11829 (2013).

Due to the severity of radical prostatectomy, recent studies have reported on focal therapy in which a portion of the prostate is preserved, although the efficacy of focal therapy of prostate cancer and preventing cancer progression remains uncertain. Quann, et al., "Current prostate biopsy protocols cannot reliably identify patients for focal therapy; . . . ", *Int. J. Clin. Exp. Pathol.*, Vol. 3(4), pp. 401-407 (2010). Identifying, targeting, and focally destroying a specific tumor has yet to be realized (Mazzucchelli at 5159), and to date focal therapy involves ablation of large portions, (e.g., hemiablation), of the prostate. It therefore was not heretofore known or expected that treating a low grade low risk unifocal prostate cancer tumor by targeting just the unifocal tumor would be effective in reducing cancer incidence, cancer grade, and cancer progression (worsening) throughout the entire lobe in which the unifocal tumor was located. As a consequence, the clinical trials in which FT was assessed to treat only the unifocal prostate cancer was not designed, and not expected to be effective in treating the lobe of the prostate in which the unifocal tumor was located.

A common technique used in identifying and monitoring prostate cancer is assessing PSA levels in conjunction with biopsy evaluation. Typical biopsy of the prostate usually involves taking numerous samples through the prostate gland, and assessing the tissue using a Gleason Score. The Gleason Score measures how abnormal a cancer cell looks like under a microscope and is a good indicator of how quickly the cells are likely to grow and spread. The Gleason Score is calculated by adding together the two grades of cancer that make up the largest areas of the biopsied tissue sample, and is often represented as two numbers, such as 3+3, along with the total score, such as 6. The following table provides a classification of the groups of prostate cancer and the associated risks:

| Risk Group | ISUP Grade Group | Gleason Score |
|---|---|---|
| Low | Grade Group 1 | Gleason Score ≤6 |
| Intermediate Favorable | Grade Group 2 | Gleason Score 7 (3 + 4) |
| Intermediate Unfavorable | Grade Group 3 | Gleason Score 7 (4 + 3) |
| High | Grade Group 4 | Gleason Score 8 |
| High | Grade Group 5 | Gleason Score 9-10 |

For low grade low risk localized (T1c) prostate cancer in which the Gleason Score is ≤6, Active Surveillance (AS) is the ordinary course of treatment. This is because, while some may very well mature to high risk cancer requiring radical prostatectomy (e.g., Gleason Score ≥3), many do not. As noted above, up to about 35% of prostates surgically removed only have low grade low risk localized (T1c) prostate cancer. Accordingly, those patients who had their prostates surgically removed but still did not have high risk cancerous tumors needlessly suffered the deleterious effects of radical prostatectomy surgery. Accordingly, the typical standard of care is that, when the Gleason Score is 7 or above, especially when the primary pattern is 4, corrective measures are taken, either by removing a large portion of the prostate, chemotherapy or radiation, or a radical prostatectomy. It therefore would be desirable to discover a safe and effective manner of treating prostate cancer patients in the low and/or low and intermediate risk groups by focal treatment of a single foci, in which case the treatment is effective in ameliorating, reducing, and/or preventing the progression of the cancer throughout the prostate lobe in which the single foci was located.

Throughout this description, including the foregoing description of related art, any and all publicly available documents described herein, including any and all U.S. patent published patent applications, are specifically incorporated by reference herein in their entirety. The foregoing description of related art is not intended in any way as an admission that any of the documents described therein, including pending U.S. patent applications, are prior art to the present disclosure. Moreover, the description herein in any disadvantages associated with the described products, methods, and/or apparatus, is not intended to limit the embodiments. Indeed, aspects of the embodiments may include certain features of the described products, methods, and/or apparatus without suffering from their described disadvantages.

SUMMARY OF THE EMBODIMENTS

There remains a need in the art for new, less toxic, and less frequent, and less invasive treatments for preventing or reducing the progression or incidence of prostate cancer. There also remains a need in the art for such treatments that reduce the incidence of multifocal prostate cancer at least in the lobe (or hemisphere) in which the initially treated foci were located. The embodiments satisfy these needs.

This disclosure is premised in part on the discovery that pharmaceutically active ingredients capable of inducing necrosis of the low grade, low risk, localized prostate cancer tumor are capable of being administered to a single low grade, low risk prostate cancer foci or tumor (i.e., Gleason Score ≤6), but yet have an unexpected effect of reducing multifocal cancer incidence, reducing multifocal cancer grade, and reducing multifocal progression (worsening) in the prostate lobe in which the low grade, low risk, localized prostate cancer tumor was located. Suitable pharmaceutically active ingredients capable of inducing necrosis of such tumors, include, for example, fexapotide triflutate, (FT), a peptide described by the amino acid sequence Ile-Asp-Gln-Gln-Val-Leu-Ser-Arg-Ile-Lys-Leu-Glu-Ile-Lys-Arg-Cys-Leu, Zytiga (abiraterone acetate), Apalutamide, abazitaxel, Casodex (Bicalutamide), Eligard and Lupron, (Leuprolide Acetate), Erleada (Apalutamide), Firmagon (Degarelix), Flutamide, Goserelin Acetate, Jevtana (Cabazitaxel), Mitoxantrone Hydrochloride, Nilandron (Nilutamide), Provenge (Sipuleucel-T), Sipuleucel-T, Taxotere (Docetaxel), Xofigo (Radium 223 Dichloride), Xtandi (Enzalutamide), Zoladex (Goserelin Acetate), and mixtures and combinations thereof. Such administration was found, after several years of ongoing follow up, to be effective in reducing cancer incidence, reducing cancer grade, and reducing cancer progression (worsening) in the prostate lobe (hemi-prostate) where the initial unifocal tumor was located and treated. The embodiments therefore are capable of vastly improving the quality of life of many men suffering from prostate cancer that would have otherwise undergone a more aggressive treatment, like ablation of a large portion of the prostate, chemotherapy, radiation, or radical prostatectomy.

Some embodiments are directed to methods of reducing cancer incidence, reducing cancer grade, and reducing cancer progression (worsening) in mammals having low grade or at low risk of prostate cancer (i.e., Gleason Score ≤6) by administering to the mammal a therapeutically effective amount of a composition comprising at least one pharmaceutically active ingredient capable of inducing necrosis of the low grade, low risk, localized prostate cancer tumor. The method includes administering a therapeutically effective amount of the composition to a single cancerous foci (unifocal tumor) in the prostate of the mammal, and reducing treatment side hemi-prostate Gleason grade increase by an amount of from about 15% to about 100%, when compared to active surveillance, when measured at least 18 months after treatment.

The compositions can be administered intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc.

In another embodiment, the composition includes a therapeutically effective amount of FT that is administered in an amount ranging from about 2.0 mg to about 20 mg. The methods also include administering a therapeutically effective amount of FT to a single cancerous foci (unifocal tumor) in the prostate of the mammal, and reducing the percentage of mammals exhibiting ≥1 new focus in the in the prostate lobe where the original foci was treated with an increase in Gleason grade primary pattern (new multifocal with Gleason primary pattern ≥4) increase by an amount of from about 50% to about 100%, when compared to active surveillance, when measured at least 18 months after treatment, or from about 45% to about 100%, when compared to active surveillance, when measured at least 36 months after treatment, or from about 45% to about 100%, when compared to active surveillance, when measured at least 48 months after treatment. In another embodiment, the method reduces treatment side hemi-prostate Gleason grade increase by an amount of from about 45% to about 70%, when compared to active surveillance, when measured at least 36 months after treatment. In another embodiment, the method includes administering a therapeutically effective amount of FT to a single cancerous foci (unifocal tumor) in the prostate of the mammal, and reducing the percentage of mammals exhibiting ≥1 new focus in the prostate lobe where the original foci was treated with an increase in Gleason grade (new multifocal with Gleason upgrade) by an amount of from about 40% to about 100%, when compared to active surveillance, when measured at least 18 months after treatment, or from about 50% to about 90%, when compared to active surveillance, when measured at least 36 months after treatment, or from about 15% to about 80%, when compared to active surveillance, when measured at least 48 months after treatment.

In another embodiment, the method includes administering a therapeutically effective amount of FT to a single cancerous foci (unifocal tumor) in the prostate of the mammal, and reducing the percentage of mammals having conventional cancer treatment (surgery, radiotherapy, or chemotherapy), and exhibiting ≥1 new focus in the prostate lobe where the original foci was treated with an increase in Gleason grade (new multifocal with Gleason upgrade) by an amount of from about 40% to about 100%, when compared to active surveillance, when measured at least 18 months after treatment, or from about 50% to about 90%, when compared to active surveillance, when measured at least 36 months after treatment, or from about 15% to about 80%, when compared to active surveillance, when measured at least 48 months after treatment. The methods also include administering a therapeutically effective amount of FT to a single cancerous foci (unifocal tumor) in the prostate of the mammal, and reducing the percentage of mammals having conventional cancer treatment (surgery, radiotherapy, or chemotherapy), and exhibiting ≥1 new focus in the in the prostate lobe where the original foci was treated with an increase in Gleason grade primary pattern (new multifocal with Gleason primary pattern 4) by an amount of from about 65% to about 100%, when compared to active surveillance, when measured at least 18 months after treatment, or from about 65% to about 100%, when compared to active surveillance, when measured at least 36 months after treatment, or from about 60% to about 100%, when compared to active surveillance, when measured at least 48 months after treatment.

Both the foregoing general description and the following detailed description are exemplary and explanatory and are intended to provide further explanation of the embodiments as claimed. Other objects, advantages, and features will be readily apparent to those skilled in the art from the following detailed description of the embodiments.

DETAILED DESCRIPTION OF THE PREFERRED EMBODIMENTS

Before the present proteins, nucleotide sequences, peptides, compositions, active agents, etc., and methods are described, it is understood that this invention is not limited to the particular methodology, protocols, cell lines, vectors, and reagents described, as these may vary. It also is to be understood that the terminology used herein is for the purpose of describing particular embodiments only, and is not intended to limit the scope of the present embodiments which will be limited only by the appended claims.

Terms and phrases used herein are defined as set forth below unless otherwise specified. Throughout this description, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Amino acids and amino acid residues described herein may be referred to according to the accepted one or three-letter code provided in the table below.

TABLE 1

| Three-Letter Amino Acid | One-Letter Symbol | Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The expression "pharmaceutically active ingredients capable of inducing necrosis of such tumors" denotes, for example, fexapotide triflutate, (FT), a peptide described by the amino acid sequence Ile-Asp-Gln-Gln-Val-Leu-Ser-Arg-Ile-Lys-Leu-Glu-Ile-Lys-Arg-Cys-Leu, ZYTIGA® (abiraterone acetate), EARLEADA® (apalutamide), abazitaxel, CASODEX® (Bicalutamide), ELIGARD® and LUPRON®, (Leuprolide Acetate), FIRMAGON® (Degarelix), flutamide, JEVTANA® (Cabazitaxel), mitoxantrone hydrochloride, NILANDRON® (Nilutamide), PROVENGE® (Sipuleucel-T), TAXOTERE® (Docetaxel), XOFIGO® (Radium 223 Dichloride), XTANDI® (Enzalutamide), ZOLADEX® (Goserelin Acetate), and mixtures and combinations thereof. Fexapotide Triflutate ("FT"), as it is used herein, denotes a 17-mer peptide having the amino acid sequence: Ile-Asp-Gln-Gln-Val-Leu-Ser-Arg-Ile-Lys-Leu-Glu-Ile-Lys-Arg-Cys-Leu (SEQ ID NO. 1). FT is disclosed in U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031. The disclosures of these patents and published applications are incorporated by reference herein in their entirety.

FT is represented by:

SEQ ID NO. 1:
IDQQVLSRIKLEIKRCL or

Ile-Asp-Gln-Gln-Val-Leu-Ser-Arg-Ile-Lys-Leu-Glu-Ile-Lys-Arg-Cys-Leu.

The term "fragment" refers to a protein or polypeptide that consists of a continuous subsequence of the amino acid sequence of a protein or peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same protein or peptide, with a contiguous amino acid sequence in common or not, joined together, either directly or through a linker. A person having ordinary skill in the art will be capable of selecting a suitable fragment for use in the embodiments without undue experimentation using the guidelines and procedures outlined herein.

The term "variant" refers to a protein or polypeptide in which one or more amino acid substitutions, deletions, and/or insertions are present as compared to the amino acid sequence of an protein or peptide and includes naturally occurring allelic variants or alternative splice variants of an protein or peptide. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, Sequence Analysis in Molecular Biology, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 2 below.

TABLE 2

| Conservative Amino Acid Substitutions | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |

TABLE 2-continued

| Conservative Amino Acid Substitutions |
|---|
| cysteine |
| glycine |
| alanine |
| valine |
| praline |
| methionine |
| leucine |
| isoleucine |

Table 3 sets out another scheme of amino acid substitution:

TABLE 3

| Original Residue | Substitutions |
|---|---|
| Ala | gly; ser |
| Arg | Lys |
| Asn | gln; his |
| Asp | Glu |
| Cys | Ser |
| Gln | Asn |
| Glu | Asp |
| Gly | ala; pro |
| His | asn; gln |
| Ile | eu; val |
| Leu | ile; val |
| Lys | arg; gln; glu |
| Met | leu; tyr; ile |
| Phe | met; leu; tyr |
| Ser | Thr |
| Thr | Ser |
| Trp | Tyr |
| Tyr | trp; phe |
| Val | ile; leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. For example, a cysteine residue may be added at both the amino and carboxy terminals of a peptide in order to allow the cyclisation of the peptide by the formation of a di-sulphide bond. The term "variant" also encompasses polypeptides that have the amino acid sequence of a peptide with at least one and up to 25 or more additional amino acids flanking either the 3' or 5' end of the peptide.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins or peptides. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid sidechains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, Proteins—Structure And Molecular Properties, 2nd Ed., T. E. Creighton, W. H. Freeman and Company, New York (1993) and Wold, F., "Posttranslational Protein Modifications: Perspectives and Prospects," pgs. 1-12 in Posttranslational Covalent Modification Of Proteins, B. C. Johnson, Ed., Academic Press, New York (1983); Seifter et al., Meth. Enzymol. 182:626-646 (1990) and Rattan et al., "Protein Synthesis: Posttranslational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein that is at least 60 percent identical in its amino acid sequence of a peptide as determined by standard methods that are commonly used to compare the similarity in position of the amino acids of two polypeptides. The degree of similarity or identity between two proteins can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M Stockton Press, New York, 1991; and Carillo H. and Lipman, D., SIAM, J. Applied Math., 48:1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., Nucleic Acids Research, 12(1): 387 (1984)), BLASTP, BLASTN, and FASTA, Atschul, S. F. et al., J. Molec. Biol., 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol., 215: 403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al. in: Atlas of Protein Sequence and Structure, vol. 5, supp.3 for the PAM250 comparison matrix; see Henikoff et al., Proc. Natl. Acad. Sci USA, 89:10915-10919 for the BLOSUM 62 comparison matrix) also may be used by the algorithm. The percent identity then is calculated by the algorithm. Homologues will typically have one or more amino acid substitutions, deletions, and/or insertions as compared with the comparison protein or peptide, as the case may be.

The term "fusion protein" refers to a protein where one or more peptides are recombinantly fused or chemically conjugated (including covalently and non-covalently) to a protein such as (but not limited to) an antibody or antibody fragment like an Fab fragment or short chain Fv. The term "fusion protein" also refers to multimers (i.e. dimers, trimers, tetramers and higher multimers) of peptides. Such multimers comprise homomeric multimers comprising one peptide, heteromeric multimers comprising more than one peptide, and heteromeric multimers comprising at least one peptide and at least one other protein. Such multimers may be the result of hydrophobic, hyrdrophilic, ionic and/or covalent associations, bonds or links, may be formed by cross-links using linker molecules or may be linked indirectly by, for example, liposome formation The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

The peptide mimetics of the embodiments are preferably substantially similar in both three-dimensional shape and biological activity to the peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala$_1$-Peptide T Binding", Smith C. S. et al., Drug Development Res., 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the peptide by pseudopeptide bonds that confer resistance to proteolysis.

A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", Escom, Leiden (1990), pp. 722-773) and Dalpozzo, et al. (1993), Int. J. Peptide Protein Res., 41:561-566, incorporated herein by reference). According to this modification, the amino acid sequences of the peptides may be identical to the sequences of a peptide described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), Int. J. Peptide Protein Res., 41:181-184, incorporated herein by reference in its entirety).

Thus, the amino acid sequences of these peptides may be identical to the sequences of a peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of peptides represent another class of peptide mimetics that retain the important structural determinants for biological activity, yet eliminate the peptide bonds, thereby conferring resistance to proteolysis (Simon, et al., 1992, Proc. Natl. Acad. Sci. USA, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the peptides may be replaced with the N-substituted glycine corresponding to the replaced amino acid.

The term "peptide mimetic" or "mimetic" also includes reverse-D peptides and enantiomers as defined below.

The term "reverse-D peptide" refers to a biologically active protein or peptide consisting of D-amino acids arranged in a reverse order as compared to the L-amino acid sequence of a peptide. Thus, the carboxy terminal residue of an L-amino acid peptide becomes the amino terminal for the D-amino acid peptide and so forth. For example, the peptide, ETESH, becomes $H_d S_d E_d T_d E_d$, where $E_d$, $H_d$, $S_d$, and $T_d$ are the D-amino acids corresponding to the L-amino acids, E, H, S, and T respectively.

The term "enantiomer" refers to a biologically active protein or peptide where one or more the L-amino acid residues in the amino acid sequence of an peptide is replaced with the corresponding D-amino acid residue(s).

A "composition" as used herein, refers broadly to any composition containing a recited peptide or amino acid sequence and, optionally an additional active agent. The composition may comprise a dry formulation, an aqueous solution, or a sterile composition. Compositions comprising peptides may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g. sodium dodecyl sulfate (SDS), and other components, e.g., Denhardt's solution, dry milk, salmon sperm DNA, etc.

The expression "low grade prostate cancer" denotes prostate cancer presenting a biopsy of prostate tissue, i.e., a single foci or multiple foci, having the highest Gleason grade of ≤6, or 3+3. The expression "low grade unifocal prostate cancer" denotes a single cancerous focus having a Gleason grade of ≤6, or 3+3 that was detected by biopsy. It will be understood that biopsies procedures, which often take numerous samples from the prostate gland, do not sample the entire gland and consequently, there may be other foci present that were not detected. The expression "progression of prostate cancer" typically denotes a higher Gleason grade in any single focus (the highest grade in all biopsies taken together is the grade), but also denotes greater amounts of cancer in the biopsy (i.e. a higher percentage of cancer in a given biopsy focus if it gets past 50% for example; or more foci positive for cancer). For example, if a patient proceeds from at one point in time with one positive core sample having 5% tumor, to at a later point in time, having 5 cores with each having 40% tumor (all of same Gleason grade), this would be considered progression, although it would not be "Gleason grade progression." On the other hand, "Gleason grade progression" would be present if a patient proceeded from 4 cores of Grade 6 each with 40% tumor, and then subsequently had only one positive core with 5% tumor, but Gleason grade 7, then that progression would be considered "Gleason grade progression."

When referring to a "biopsy", those skilled in the art will appreciate that a typical biopsy consists of multiple "quadrant" samples, generally at least 10 or 12, sampling all areas of the gland (left and right; apex, mid, and base for each; and medial and lateral for each, and transition L and R), thus equaling 14 zones. Therefore a reference to "biopsy" or "a biopsy" denotes 10-15 biopsies at the same time, with each being reported separately.

In an embodiment in which an additional active agent is used together with composition, the expression "active agent" is used to denote any agent capable of removing unwanted cellular proliferations and/or tissue growth. Suitable active agents may include, but are not limited to: (i) anti-cancer active agents (such as alkylating agents, topoisomerase I inhibitors, topoisomerase II inhibitors, RNA/DNA antimetabolites, and antimitotic agents); (ii) active agents for treating benign growths such as anti-acne and anti-wart active agents; (iii) antiandrogen compounds, (cyproterone acetate (1α, 2ß-methylene-6-chloro-17α-acetoxy-6-dehydroprogesterone) Tamoxifen, aromatase inhibitors); (iv) alpha1-adrenergic receptor blockers (tamsulosin, terazosin, doxazosin, prazosin, bunazosin, indoramin, alfulzosin, silodosin); (v) 5α-reductase inhibitors (finasteride, dutasteride); (vi) phosphodiesterase type 5 (PDE5) inhibitors (tadalafil) and combinations thereof.

The embodiments are directed to methods of administering to a low grade, low risk, localized prostate cancer tumor a composition comprising at least one pharmaceutically active ingredient capable of inducing necrosis of the low grade, low risk, localized prostate cancer tumor, and reducing prostate cancer incidence, reducing prostate cancer grade, and reducing prostate cancer progression (worsening) in the entire hemi-prostate where the initial unifocal tumor was located and treated. Suitable pharmaceutically active ingredients capable of inducing necrosis of such tumors, include, for example, fexapotide triflutate, (FT), a peptide described by the amino acid sequence Ile-Asp-Gln-Gln-Val-Leu-Ser-Arg-Ile-Lys-Leu-Glu-Ile-Lys-Arg-Cys-Leu, ZYTIGA® (abiraterone acetate), EARLEADA® (apalutamide), abazitaxel, CASODEX® (Bicalutamide), ELIGARD 8 and LUPRON®, (Leuprolide Acetate), FIRMAGON® (Degarelix), flutamide, JEVTANA® (Cabazitaxel), mitoxantrone hydrochloride, NILANDRON® (Nilutamide), PROVENCE® (Sipuleucel-T), TAXOTERE® (Docetaxel), XOFIGO® (Radium 223 Dichloride), XTANDI® (Enzalutamide), ZOLADEX® (Goserelin Acetate), and mixtures and combinations thereof. In an embodiment, the compositions are administered more than once. The embodiments therefore provide a method of reducing prostate cancer incidence, grade, and progression in a minimally invasive manner, by administering the compositions to mammals that typically would not be treated. It is generally accepted that mammals with low grade unifocal or multifocal prostate cancer having Gleason grade ≤6 undergo active surveillance (AS), or no treatment. See, e.g., Ahmed, et al., "Do Low-Grade and Low-Volume Prostate Cancers Bear the Hallmarks of Malignancy," available on-line at https://www.thelancet.com/jornals/lanonc/article/PIIS1470-2045(12)70388-1/fulltext, pp e509-e517 (2012).

The inventor unexpectedly discovered that administration of such compositions to a single focus of low grade, low risk, localized prostate cancer tumor significantly reduced prostate cancer incidence, prostate cancer grade, and prostate cancer progression in the prostate lobe in which the initially treated tumor was located. The methods of the embodiments therefore provide a non-invasive method of reducing multifocal prostate cancer, when compared to radical prostatectomy, or even focal ablation, excision, chemotherapy, or radiation. Even active surveillance requires multiple and repeated prostate biopsies and evaluation, and places a large burden on the health care system. Accordingly, the methods described herein are useful in retarding the incidence, occurrence, and progression of prostate cancer in a non-invasive manner.

In contrast to the published literature, mammals treated with the compositions of the present invention exhibited a dramatic decrease in the incidence of prostate cancer, a dramatic decrease in Gleason grade increase, and a dramatic decrease in prostate cancer progression. The method of the embodiments can reduce treatment side hemi-prostate Gleason grade increase, when compared to active surveillance controls, when measured at least 18 months after treatment, by an amount of from about 15% to about 100%, or from about 20% to about 95%, or from about 25% to about 88%, or from about 30% to about 85%, or from about 40% to about 80%, or from about 45% to about 95%, or from about 45% to about 80%, or any value therebetween, when compared to active surveillance control at 18 months, or 36 months, or 48 months, or 60 months.

The method of the embodiments can reduce multifocal prostate cancer in the lobe (or hemi-prostate) in which the foci were initially treated with Gleason upgrade (patients with >=1 new focus in treated lobe or hemi-prostate with increased Gleason grade), when compared to active surveillance controls, when measured at least 18 months after treatment, by an amount of from about 40% to about 100%, or from about 50% to about 90%, or from about 60% to about 80%, or any value therebetween. The method of the embodiments can reduce hemi-prostate multifocal cancer with Gleason upgrade, when compared to active surveillance controls, when measured at least 36 months after treatment, by an amount of from about 50% to about 90%, or from about 50% to about 85%, or from about 50% to about 80%, or any value therebetween. The method of the embodiments can reduce hemi-prostate multifocal cancer with Gleason upgrade, when compared to active surveillance controls, when measured at least 48 months after treatment, by an amount of from about 15% to about 80%, or from about 15% to about 75%, or from about 16% to about 72%, or any value therebetween.

The method of the embodiments can reduce multifocal prostate cancer in the lobe (or hemi-prostate) in which the foci were initially treated with Gleason primary pattern ≥4 (patients with >=1 new focus in treated lobe or hemi-prostate with an increase in Gleason grade primary pattern), when compared to active surveillance controls, when measured at least 18 months after treatment, by an amount of from about 50% to about 100%, or from about 70% to about 100%, or from about 75% to about 100%, or any value therebetween. The method of the embodiments can reduce hemi-prostate multifocal cancer with Gleason primary pattern ≥4, when compared to active surveillance controls, when measured at least 36 months after treatment, by an amount of from about 45% to about 100%, or from about 70% to about 100%, or from about 75% to about 100%, or any value therebetween. The method of the embodiments can reduce hemi-prostate multifocal cancer with Gleason upgrade (patients with >=1 new focus in entire prostate with increased Gleason grade), when compared to active surveillance controls, when measured at least 48 months after treatment, by an amount of from 45% to about 100%, or from about 60% to about 100%, or from about 70% to about 100%, or any value therebetween.

The method of the embodiments can reduce the percentage of mammals having conventional cancer treatment (surgery, radiotherapy, or chemotherapy), and having multifocal prostate cancer in the lobe (or hemi-prostate) in which the foci were initially treated with Gleason upgrade (cancer treatment with new multifocal with increased Gleason grade in the hemi-prostate), when compared to active surveillance controls, when measured at least 18 months after treatment, by an amount of from about 40% to about 100%, or from about 50% to about 90%, or from about 60% to about 75%, or any value therebetween. The method of the embodiments can reduce cancer treatment with new multifocal with increased Gleason grade in the hemi-prostate, when compared to active surveillance controls, when measured at least 36 months after treatment, by an amount of from about 50% to about 90%, or from about 55% to about 75%, or from about 50% to about 80%, or any value therebetween. The method of the embodiments can reduce cancer treatment with new multifocal with increased Gleason grade in the hemi-prostate, when compared to active surveillance controls, when measured at least 48 months after treatment, by an amount of from about 15% to about 80%, or from about 35% to about 75%, or from about 40% to about 75%, or any value therebetween.

The method of the embodiments can reduce the percentage of mammals having conventional cancer treatment (surgery, radiotherapy, or chemotherapy), and having multifocal prostate cancer in the lobe (or hemi-prostate) in which the foci were initially treated with Gleason primary pattern (cancer treatment with new multifocal and an increase in Gleason grade primary pattern in the hemi-prostate), when compared to active surveillance controls, when measured at least 18 months after treatment, by an amount of from about 65% to about 100%, or from about 70% to about 100%, or from about 75% to about 100%, or any value therebetween. The method of the embodiments can reduce cancer treatment with new multifocal and an increase in Gleason grade primary pattern in the hemi-prostate, when compared to active surveillance controls, when measured at least 36 months after treatment, by an amount of from about 65% to about 100%, or from about 70% to about 100%, or from about 75% to about 100%, or any value therebetween. The method of the embodiments can reduce cancer treatment with new multifocal and an increase in Gleason grade primary pattern in the hemi-prostate, when compared to active surveillance controls, when measured at least 48 months after treatment, by an amount of from about 60% to about 100%, or from about 65% to about 100%, or from about 75% to about 100%, or any value therebetween.

Any mammal can benefit from use of the invention, including humans, mice, rabbits, dogs, sheep and other livestock, any mammal treated or treatable by a veterinarian, zoo-keeper, or wildlife preserve employee. Preferred mammals are humans, sheep, and dogs. Throughout this description mammals and patients are used interchangeably.

It will be apparent to one of skill in the art that other smaller fragments of FT may be selected such that these peptides will possess the same or similar biological activity. Other fragments of FT may be selected by one skilled in the art such that these peptides will possess the same or similar biological activity. The term "FT" as used in the embodiments therefore encompasses these other fragments. In general, the peptides of the embodiments have at least 4 amino acids, preferably at least 5 amino acids, and more preferably at least 6 amino acids.

The embodiments also encompass methods of treatment comprising administering a composition comprising FT that includes two or more FT sequences joined together, together with an additional active agent. To the extent that FT has the desired biological activity, it follows that two or more FT sequences would also possess the desired biological activity.

FT and fragments, variants, derivatives, homologues, fusion proteins and mimetics thereof encompassed by this embodiment can be prepared using methods known to those of skill in the art, such as recombinant DNA technology, protein synthesis and isolation of naturally occurring peptides, proteins, variants, derivatives and homologues thereof. FT and fragments, variants, derivatives, homologues, fusion proteins and mimetics thereof can be prepared from other peptides, proteins, and fragments, variants, derivatives and homologues thereof using methods known to those having skill in the art. Such methods include (but are not limited to) the use of proteases to cleave the peptide, or protein into FT. Any method disclosed in, for example, U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031, can be used to prepare the FT peptide described herein. The disclosures of these patent documents are incorporated by reference herein in their entireties.

The additional active agent, if used in addition to the one or more pharmaceutically active ingredients, can be one or more active agents selected from (i) anti-cancer active agents (such as alkylating agents, topoisomerase I inhibitors, topoisomerase II inhibitors, RNA/DNA antimetabolites, and antimitotic agents); (ii) active agents for treating benign growths such as anti-acne and anti-wart active agents (salicylic acid); (iii) antiandrogen compounds, (cyproterone acetate (1α, 2ß-methylene-6-chloro-17α-acetoxy-6-dehydroprogesterone)) Tamoxifen, aromatase inhibitors); (iv) alpha1-adrenergic receptor blockers (tamsulosin, terazosin, doxazosin, prazosin, bunazosin, indoramin, alfulzosin, silodosin); (v) 5α-reductase inhibitors (finasteride, dutasteride); (vi) phosphodiesterase type 5 (PDE5) inhibitors (tadalafil) and combinations thereof. Preferably, the additional agent is an anti-cancer agent and specifically an agent useful in treating prostate cancer.

Therapeutic compositions described herein may comprise an amount of pharmaceutically active ingredient in admixture with a pharmaceutically acceptable carrier. In some alternative embodiments, the additional active agent can be administered in the same composition with the pharmaceutically active ingredient, and in other embodiments, the composition comprising the pharmaceutically active ingredient is administered as an injection, whereas the additional active agent is formulated into an oral medication (gel, capsule, tablet, liquid, etc.). The carrier material may be water for injection, preferably supplemented with other materials common in solutions for administration to mammals. Typically, when the pharmaceutically active ingredient is FT, it will be administered in the form of a composition comprising the purified FT peptide (or chemically synthesized FT peptide) in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Compositions of the embodiments also may comprise buffers known to those having ordinary skill in the art with an appropriate range of pH values, including Tris buffer of about pH 7.0-8.5, or acetate buffer of about pH 4.0-5.5, which may further include sorbitol or a suitable substitute therefor.

Solid dosage forms for oral administration include but are not limited to, capsules, tablets, pills, powders, and granules. In such solid dosage forms, the additional active agent, and/or the pharmaceutically active ingredient can be admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as acetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active ingredients in the compositions of the embodiments may be varied to obtain an amount of the pharmaceutically active ingredient and additional active agent that is effective to obtain a desired therapeutic response for a particular composition. The selected dosage level therefore depends upon the desired therapeutic effect, the route of administration, the desired duration of treatment, and other factors.

With mammals, including humans, the effective amounts can be administered on the basis of body surface area. The interrelationship of dosages for animals of various sizes, species and humans (based on mg/M$^2$ of body surface) is described by E. J. Freireich et al., Cancer Chemother. Rep., 50 (4):219 (1966). Body surface area may be approximately determined from the height and weight of an individual (see e.g., Scientific Tables, Geigy Pharmaceuticals, Ardsley, N.Y. pp. 537-538 (1970)).

It will be understood that the specific dose level for any particular patient will depend upon a variety of factors including the body weight, general health, sex, diet, time and route of administration, potency of the administered drug, rates of absorption and excretion, combination with other drugs and the severity of the particular disease being treated.

A method of administering a composition comprising the pharmaceutically active ingredient according to the embodiments includes, but is not limited to, administering the compositions intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transrectally, transperitoneally, transdermally, via an aerosol, infusion, bolus injection, implantation device, sustained release system etc. Any method of administration disclosed in, for example, U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031, can be used.

Use of FT is a preferred embodiment. FT is a new molecular entity which in vitro stimulates caspase pathways (activation of caspases 7, 8, and 10, caspase recruitment domains 6, 11, and 14, and DIABLO), tumor necrosis factor pathways (activation of TNF1, TNFSF6, TNFSF8, TNFSF9, CD70 ligands, and TNFRSF19L, TNFRSF25, TRAF2, TRAF3, TRAF4, TRAF6 receptors), and BCL pathways (activation of BIK, HRK, BCL2L10 and BCL3) in prostate glandular epithelial cells, based on tissue culture genetic array data. FT selectively causes loss of cell membrane integrity, mitochondrial metabolic arrest, depletion of RNA, DNA lysis and aggregation, and cell fragmentation and cell loss. The apoptotic process leads to typical ultrastructural progressive changes of membranous disruption and swelling, progressively deepening nuclear invaginations with eventual membranous bleb formations and cell death and fragmentation into apoptotic bodies. Histologically, typical apoptotic changes with positive immunohistochemical staining of markers for apoptosis are found throughout the injected areas for up to several weeks after treatment.

FT has been extensively tested in patients with BPH. The compound and placebo controls have been administered by the transrectal route in over 1700 procedures in 9 human clinical trials. In these large long-term clinical trials in men with BPH, FT was administered in a concentration of 0.25 mg/ml (2.5 mg of FT—amounting to administration to about 15-20% of the gland by volume). See, e.g., Shore, et al., "The potential for NX-1207 in benign prostatic hyperplasia: an update for clinicians," Ther Adv. Chronic Dis., 2(6), pp. 377-383 (2011). It therefore is preferred that compositions comprising FT include at least 2.5 mg of FT, and can be administered in amounts of up to 25 mg of FT in a single administration. In another embodiment, FT is administered in an amount within the range of from about 2.5 mg to about 20 mg, or from about 2.5 mg to about 15 mg. In an embodiment, FT is administered in an amount of 15 mg.

The following examples are provided to illustrate the present embodiments. It should be understood, however, that the embodiments are not to be limited to the specific conditions or details described in these examples. Throughout the specification, any and all references to a publicly available document, including a U.S. patent, are specifically incorporated by reference. In particular, the embodiments expressly incorporate by reference the examples contained in U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031, each of which reveal that certain peptides specified therein are effective agents for causing cell death in vivo in normal rodent muscle tissue, subcutaneous connective tissue, dermis and other tissue.

EXAMPLES

In a series of clinical studies a total of 146 men with low grade prostate cancer (Gleason grade 6) were treated in the following manner. Patients were randomized and treated with a transrectal intraprostatic single injection of a composition comprising 2.5 mg FT (n=49), or a composition comprising 15 mg FT (n=48), or were subject to control active surveillance (n=49). After the first follow-up biopsy at 45 days post-randomization, 18 patients in the control active surveillance group crossed over to a single administration of a composition comprising 2.5 mg FT. Patients were followed for 5 years including biopsies at baseline, 45 days, 18, 36, and 60 months, and urological evaluations with PSA every 6 months. Patients with Gleason grade increase or who elected surgical or radiotherapeutic intervention exited the study and were still included in the data analysis. Percentage of normal biopsies in the baseline focus quadrant and median tumor grade and volume were assessed; progression was measured by clinical and pathological outcomes including Gleason grade in the entire prostate sampled as well as for the treated prostate lobe. Interventions associated with Gleason grade increase as well as total incidence for any intervention was assessed.

Example 1

This example evaluated the percentage of patients who exhibited greater than one new focus (i.e., went from unifocal to multifocal) in the hemi-prostate in which the initial unifocal tumor was treated, in which the new focus had an increase in Gleason grade total score ("hemi-prostate multifocal cancer with Gleason upgrade"). The data in the tables below for the times of follow up represent the percentage of patients who exhibited progression or worsening. The results are shown in Table 3 below:

TABLE 3

| | Time from treatment and % improvement | | | | | |
|---|---|---|---|---|---|---|
| Treatment | <= 18 mos | % Imp. | <= 36 mos | % Imp. | <= 48 mos | % Imp. |
| FT 15 mg | 5.7 | 69.7 | 9.1 (p = 0.049) | 74.5 | 13.3 | 70.8 |
| FT 2.5 mg | 8.6 | 54.26 | 16.7 | 53.2 | 42.9 | 5.7 |
| Pooled FT | 7.1 | 62.2 | 13.0 (p = 0.0549) | 63.6 | 27.6 | 39.3 |
| Control | 18.8 | | 35.7 | | 45.5 | |

The results from example 1 reveal that the embodiments can reduce the percentage of patients who had multifocal prostate cancer in the lobe (or hemi-prostate) in which the foci were initially treated with Gleason upgrade (patients with >=1 new focus in treated lobe or hemi-prostate with increased Gleason grade), when compared to active surveillance controls, when measured at least 18 months after treatment, by an amount of from about 40% to about 100%, or from about 50% to about 90%, or from about 60% to about 80%, or any value therebetween. The method of the embodiments can reduce the percentage of patients who had hemi-prostate multifocal cancer with Gleason upgrade, when compared to active surveillance controls, when measured at least 36 months after treatment, by an amount of from about 50% to about 90%, or from about 50% to about 85%, or from about 50% to about 80%, or any value therebetween. The method of the embodiments can reduce the percentage of patients who had hemi-prostate multifocal cancer with Gleason upgrade, when compared to active surveillance controls, when measured at least 48 months after treatment, by an amount of from about 15% to about 80%, or from about 15% to about 75%, or from about 16% to about 72%, or any value therebetween.

Example 2

This example evaluated the percentage of patients who exhibited greater than one new focus (i.e., went from unifocal to multifocal) in the hemi-prostate in which the initial unifocal tumor was treated, in which the new focus had an increase in Gleason grade primary pattern 4 ("hemi-prostate multifocal cancer with increase in Gleason primary pattern"). The results are shown in Table 4 below:

TABLE 4

| | Time from treatment and % improvement | | | | | |
|---|---|---|---|---|---|---|
| Treatment | <= 18 mos | % Imp. | <= 36 mos | % Imp. | <= 48 mos | % Imp. |
| FT 15 mg | 2.9 | 76.8 | 4.5 | 79 | 6.7 | 75.5 |
| FT 2.5 mg | 0 (p = 0.033) | 100 | 0 (p = 0.018) | 100 | 0 (p = 0.037) | 100 |
| Pooled FT | 1.4 (p = 0.03) | 88.8 | 2.2 (p = 0.011) | 89.7 | 3.4 (p = 0.025) | 87.5 |
| Control | 12.5 | | 21.4 | | 27.3 | |

The results from example 2 reveal that the embodiments can reduce the percentage of patients who had hemi-prostate multifocal cancer with increase in Gleason primary pattern, when compared to active surveillance controls, when measured at least 18 months after treatment, by an amount of from about 50% to about 100%, or from about 70% to about 100%, or from about 75% to about 100%, or any value therebetween. The method of the embodiments can reduce the percentage of patients who had hemi-prostate multifocal cancer with increase in Gleason primary pattern, when compared to active surveillance controls, when measured at least 36 months after treatment, by an amount of from about 45% to about 100%, or from about 70% to about 100%, or from about 75% to about 100%, or any value therebetween. The method of the embodiments can reduce the percentage of patients who had hemi-prostate multifocal cancer with increase in Gleason primary pattern, when compared to active surveillance controls, when measured at least 48 months after treatment, by an amount of from 45% to about 100%, or from about 60% to about 100%, or from about 70% to about 100%, or any value therebetween.

Example 3

This example evaluated the percentage of patients who had conventional cancer treatment (e.g., surgery, radiotherapy, and/or chemotherapy), and who and who had multifocal prostate cancer in the lobe (or hemi-prostate) in which the foci were initially treated with Gleason upgrade (cancer treatment with new multifocal with increased Gleason grade in the hemi-prostate). The results are shown in Table 5 below:

TABLE 5

| | Time from treatment and % improvement | | | | | |
|---|---|---|---|---|---|---|
| Treatment | <= 18 mos | % Imp. | <= 36 mos | % Imp. | <= 48 mos | % Imp. |
| FT 15 mg | 5.1 | 67.7 | 7.1 | 69.8 | 8.3 | 73.5 |
| FT 2.5 mg | 4.9 | 69 | 10 | 57.4 | 17.4 | 44.4 |
| Pooled FT | 5 | 68.4 | 8.6 | 63.4 | 12.8 | 59.1 |
| Control | 15.8 | | 23.5 | | 31.3 | |

The results from example 3 reveal that the embodiments can reduce the percentage of patients who had cancer treatment with new multifocal cancer with Gleason upgrade in the hemi-prostate, when compared to active surveillance controls, when measured at least 18 months after treatment, by an amount of from about 40% to about 100%, or from about 50% to about 90%, or from about 60% to about 75%, or any value therebetween. The method of the embodiments can reduce the percentage of patients who had cancer treatment with new multifocal with increased Gleason grade in the hemi-prostate, when compared to active surveillance controls, when measured at least 36 months after treatment, by an amount of from about 50% to about 90%, or from about 55% to about 75%, or from about 50% to about 80%, or any value therebetween. The method of the embodiments can reduce the percentage of patients who had cancer treatment with new multifocal with increased Gleason grade in the hemi-prostate, when compared to active surveillance controls, when measured at least 48 months after treatment, by an amount of from about 15% to about 80%, or from about 35% to about 75%, or from about 40% to about 75%, or any value therebetween.

Example 4

This example evaluated the percentage of patients having conventional cancer treatment (surgery, radiotherapy, or chemotherapy), and having multifocal prostate cancer in the lobe (or hemi-prostate) in which the foci were initially treated with Gleason primary pattern (cancer treatment with new multifocal and an increase in Gleason grade primary pattern in the hemi-prostate). The results are shown in Table 6 below:

TABLE 6

| | Time from treatment and % improvement | | | | | |
|---|---|---|---|---|---|---|
| Treatment | <= 18 mos | % Imp. | <= 36 mos | % Imp. | <= 48 mos | % Imp. |
| FT 15 mg | 2.6 | 75.2 | 3.6 | 79.5 | 4.2 | 77.7 |
| FT 2.5 mg | 0 | 100 | 0 | 100 | 0 | 100 |
| | (p = 0.025) | | (p = 0.017) | | (p = 0.031) | |
| Pooled FT | 1.3 | 87.6 | 1.7 | 90.3 | 2.1 | 88.8 |
| | (p = 0.034) | | (p = 0.01) | | (p = 0.019) | |
| Control | 10.5 | | 17.6V | | 18.8 | |

The results from example 4 reveal that the embodiments can reduce the embodiments can reduce the percentage of patients who had cancer treatment with new multifocal cancer with an increase in Gleason grade primary pattern in the hemi-prostate, when compared to active surveillance controls, when measured at least 18 months after treatment, by an amount of from about 65% to about 100%, or from about 70% to about 100%, or from about 75% to about 100%, or any value therebetween. The method of the embodiments can reduce the percentage of patients who had cancer treatment with new multifocal and an increase in Gleason grade primary pattern in the hemi-prostate, when compared to active surveillance controls, when measured at least 36 months after treatment, by an amount of from about 65% to about 100%, or from about 70% to about 100%, or from about 75% to about 100%, or any value therebetween. The method of the embodiments can reduce the percentage of patients who had cancer treatment with new multifocal and an increase in Gleason grade primary pattern in the hemi-prostate, when compared to active surveillance controls, when measured at least 48 months after treatment, by an amount of from 60% to about 100%, or from about 65% to about 100%, or from about 75% to about 100%, or any value therebetween.

The results from the foregoing examples illustrate the unexpectedly superior effect of pharmaceutically active ingredients, and specifically FT, in reducing cancer incidence, reducing cancer grade, and reducing cancer progression (worsening) in the entire hemi-prostate where the initial low grade tumor was located and treated. It will be apparent to those skilled in the art that various modifications and variations can be made in the methods and compositions of the present embodiments without departing from the spirit or scope of the embodiments.

What is claimed is:

1. A method of reducing cancer incidence, reducing cancer grade, and reducing cancer progression in a mammal having a low grade unifocal prostate cancer tumor comprising:
   identifying a mammal having a low grade unifocal prostate cancer tumor; and
   administering to the low grade unifocal prostate cancer tumor of the mammal so identified, the administering by intraprostatic injection directly to the low grade unifocal prostate cancer tumor a composition comprising a therapeutically effective amount of fexapotide triflutate (FT);
   wherein administering FT to the low grade unifocal prostate cancer tumor reduces cancer incidence, reduces cancer grade, and reduces prostate cancer progression in the entire hemi-prostate where the initial low grade unifocal prostate cancer tumor was located and treated.

2. The method of claim 1, wherein the method reduces hemi-prostate Gleason grade increase by an amount of from about 15% to about 100%, when compared to active surveillance, when measured at least 18 months after treatment.

3. The method of claim 2, wherein the method reduces hemi-prostate Gleason grade increase by an amount of from about 45% to about 70%, when compared to active surveillance, when measured at least 18 months after treatment.

4. The method of claim 1, wherein the method reduces new multifocal prostate cancer with Gleason grade increase in the entire hemi-prostate where the low grade unifocal prostate cancer tumor was located by:
   a) an amount of from about 40% to about 100%, when compared to active surveillance, when measured at least 18 months after treatment;
   b) an amount of from about 50% to about 90%, when compared to active surveillance, when measured at least 36 months after treatment; and
   c) an amount of from about 15% to about 80%, when compared to active surveillance, when measured at least 48 months after treatment.

5. The method of claim 1, wherein the method reduces new multifocal prostate cancer with an increase in Gleason grade primary pattern in the entire hemi-prostate where the low grade unifocal prostate cancer tumor was located by: a) an amount of from about 50% to about 100%, when compared to active surveillance, when measured at least 18 months after treatment; b) an amount of from about 45% to about 100%, when compared to active surveillance, when measured at least 36 months after treatment; and c) an amount of from about 45% to about 100%, when compared to active surveillance, when measured at least 48 months after treatment.

6. The method of claim 1, wherein the method reduces conventional cancer treatment and new multifocal prostate cancer with Gleason grade increase in the entire hemi-prostate where the low grade unifocal prostate cancer tumor was located by: a) an amount of from about 40% to about 100%, when compared to active surveillance, when measured at least 18 months after treatment; b) an amount of from about 50% to about 90%, when compared to active surveillance, when measured at least 36 months after treatment; and c) an amount of from about 15% to about 80%, when compared to active surveillance, when measured at least 48 months after treatment.

7. The method of claim 1, wherein the therapeutically effective amount of FT is within the range of from about 2.5 mg to about 20 mg.

8. The method of claim 1, wherein the therapeutically effective amount of FT is within the range of from about 2.5 mg to about 15 mg.

9. The method of claim 1, wherein the therapeutically effective amount of FT is 15 mg.

10. The method of claim 1, wherein the method further comprising administering a composition comprising a therapeutically effective amount of an additional pharmaceutically active ingredient.

11. The method of claim 10, wherein the additional pharmaceutically active ingredient is selected from at least one of the group consisting of abiraterone acetate, apalutamide, abazitaxel, Bicalutamide, Leuprolide Acetate, Degarelix, flutamide, Cabazitaxel, mitoxantrone hydrochloride, Nilutamide, Sipuleucel-T, Docetaxel, Radium 223 Dichloride, Enzalutamide, Goserelin Acetate, and mixtures and combinations thereof.

* * * * *